(12) United States Patent
Courtney et al.

(10) Patent No.: US 10,458,925 B2
(45) Date of Patent: Oct. 29, 2019

(54) APPARATUS AND METHODS FOR INSPECTING BODIES HAVING A PLURALITY OF CHANNELS

(71) Applicant: Corning Incorporated, Corning, NY (US)

(72) Inventors: Andrew Paul Courtney, Painted Post, NY (US); Brian George Martinec, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/213,680

(22) Filed: Jul. 19, 2016

(65) Prior Publication Data

US 2017/0023493 A1    Jan. 26, 2017

Related U.S. Application Data

(60) Provisional application No. 62/196,733, filed on Jul. 24, 2015.

(51) Int. Cl.
  *G01N 21/956* (2006.01)
  *G01N 21/88* (2006.01)
  *G01N 21/84* (2006.01)

(52) U.S. Cl.
  CPC ... *G01N 21/95692* (2013.01); *G01N 21/8803* (2013.01); *G01N 21/8806* (2013.01); *G01N 2021/845* (2013.01); *G01N 2201/06126* (2013.01)

(58) Field of Classification Search
  CPC ......... G01N 21/95692; G01N 21/8803; G01N 21/8806; G01N 2201/06126; G01N 2021/845; G01N 21/956; G01N 21/88; G01B 11/16; B01D 46/0086; B25J 9/1697

See application file for complete search history.

(56) References Cited

U.S. PATENT DOCUMENTS

| | | | |
|---|---|---|---|
| 5,314,055 A * | 5/1994 | Gordon | B25J 9/1697 198/395 |
| 6,172,748 B1 * | 1/2001 | Sones | G01N 21/9054 356/237.1 |
| 6,954,268 B2 | 10/2005 | Naiki et al. | |
| 2011/0271740 A1 * | 11/2011 | Kondo | B01D 46/0086 73/28.04 |

FOREIGN PATENT DOCUMENTS

| | | | |
|---|---|---|---|
| CN | 100370243 C | 2/2008 | |
| CN | 103438821 B | * 12/2015 | ............. G01B 11/16 |
| KR | 2010071551 A | 6/2010 | |
| WO | 2012105837 A1 | 8/2012 | |

OTHER PUBLICATIONS

Graczyk, C., et al., "Characterization of wall slip in extrusion of ceramic pastes", Key Engineering Materials, vols. 206-213, p. 321-324.

* cited by examiner

*Primary Examiner* — Jamil Ahmed (57) ABSTRACT

An inspection apparatus and methods for inspecting a body having a structure of walls defining a plurality of channels, such as a honeycomb structure. An inspection apparatus may include a translucent conveyor belt and a light source oriented to direct light onto the backlight surface. The light source and the belt are arranged to convey the body while directing diffuse light into the body, whereby inspection of the inner walls of the structure may be facilitated.

19 Claims, 8 Drawing Sheets

APPARATUS AND METHODS FOR INSPECTING BODIES HAVING A PLURALITY OF CHANNELS

CROSS-REFERENCE TO RELATED APPLICATIONS

This application claims the benefit of priority of U.S. Provisional Application Ser. No. 62/196,733 filed on Jul. 24, 2015 the content of which is relied upon and incorporated herein by reference in its entirety.

FIELD

The present disclosure relates to bodies comprising a structure comprised of walls that define a plurality of channels, and in particular relates to apparatus and methods of inspecting such bodies.

The entire disclosure of any publication or patent document mentioned herein is incorporated by reference.

BACKGROUND

Bodies comprising a structure comprised of walls extending in a longitudinal direction and defining a plurality of longitudinal channels are useful in various applications. For example, porous ceramic cellular articles, having a honeycomb structure, may be used as substrates for catalytic material and/or may serve as particulate filters, such as in cleaning exhaust streams and gas streams. In some applications the body needs sufficient structural or mechanical integrity such as to withstand impact or thermal requirements.

SUMMARY

Disclosed herein are an inspection apparatus and methods for inspecting a body comprising a structure comprised of walls defining a plurality of channels. In some embodiments, the structure is a honeycomb structure. In some embodiments, the structure is comprised of a porous material. In some embodiments, the structure is comprised of a porous ceramic material. In some embodiments, the structure is comprised of ceramic material. In some embodiments, the structure further comprises catalytic material. In some embodiments, at least a portion of the catalytic material resides within the walls.

An inspection apparatus is disclosed herein for inspecting a body comprising a structure comprised of walls extending in a longitudinal direction between a first end and a second end, the walls defining a plurality of longitudinal channels extending between first and second faces disposed at the first and second ends, respectively, the system comprising: a translucent conveyor belt comprising a backlight surface and an opposing end supporting surface; and a light source oriented to direct light onto the backlight surface. The light source and the belt are arranged to convey the body while directing diffuse light into the body, whereby inspection of the inner walls of the structure may be facilitated. Preferably the apparatus further comprises a belt drive 140 is provided to control movement of the belt, such as a translation movement to convey the body atop the belt. Preferably the apparatus further comprises at least one mirror oriented to reflect an internally lighted image of a non-supported end of the body.

Also disclosed herein is a method of inspecting a body comprising a structure comprised of walls extending in a longitudinal direction between a first end and a second end, the walls defining a plurality of longitudinal channels extending between first and second faces disposed at the first and second ends, respectively, the method comprising emitting light toward the first face and into the channels to provide lighted channels, inspecting a view of the lighted channels from the second end, and moving the body in a direction orthogonal to the longitudinal direction, wherein the emitting, the inspecting, and the moving are all performed simultaneously.

Also disclosed herein is a method of inspecting a body comprising a structure comprised of walls extending in a longitudinal direction between a first end and a second end, the walls defining a plurality of longitudinal channels extending between first and second faces disposed at the first and second ends, respectively, the method comprising conveying the body on a translucent conveyor belt past a light source to introduce diffuse light into the channels to provide lighted channels, and inspecting a view of the lighted channels from the second end.

Also disclosed herein is a method of inspecting a body comprising a structure comprised of walls extending in a longitudinal direction between a first end and a second end, the walls defining a plurality of longitudinal channels extending between first and second faces disposed at the first and second ends, respectively, the method comprising conveying the body while introducing diffuse light into the channels from one end of the body to provide lighted channels, and inspecting a view of the lighted channels from the other end of the body.

Additional features and advantages are set forth in the Detailed Description that follows, and in part will be readily apparent to those skilled in the art from the description or recognized by practicing the embodiments as described in the written description and claims hereof, as well as the appended drawings. It is to be understood that both the foregoing general description and the following Detailed Description are merely exemplary, and are intended to provide an overview or framework to understand the nature and character of the claims.

BRIEF DESCRIPTION OF THE DRAWINGS

The accompanying drawings are included to provide a further understanding, and are incorporated in and constitute a part of this specification. The drawings illustrate one or more embodiment(s), and together with the Detailed Description serve to explain principles and operation of the various embodiments. The disclosure will become more fully understood from the following Detailed Description, taken in conjunction with the accompanying Figures, in which.

DETAILED DESCRIPTION

Reference is now made in detail to various embodiments of the disclosure, examples of which are illustrated in the accompanying drawings. Whenever possible, the same or like reference numbers and symbols are used throughout the drawings to refer to the same or like parts. The drawings are not necessarily to scale, and one skilled in the art will recognize where the drawings have been simplified to illustrate the key aspects of the disclosure.

The claims as set forth below are incorporated into and constitute part of this Detailed Description.

Cartesian coordinates may be shown in some of the Figures for the sake of reference and are not intended to be limiting as to direction or orientation.

In the discussion herein, the term "body comprising a structure comprised of walls that define a plurality of longitudinal channels" or "body with longitudinal channels or cells" comprises a body comprising a honeycomb structure or other matrix or web of walls, at least a portion of which are intersecting walls, such as cellular bodies or fluid treatment articles or exhaust treatment articles comprising one or more such body.

Figure 1:
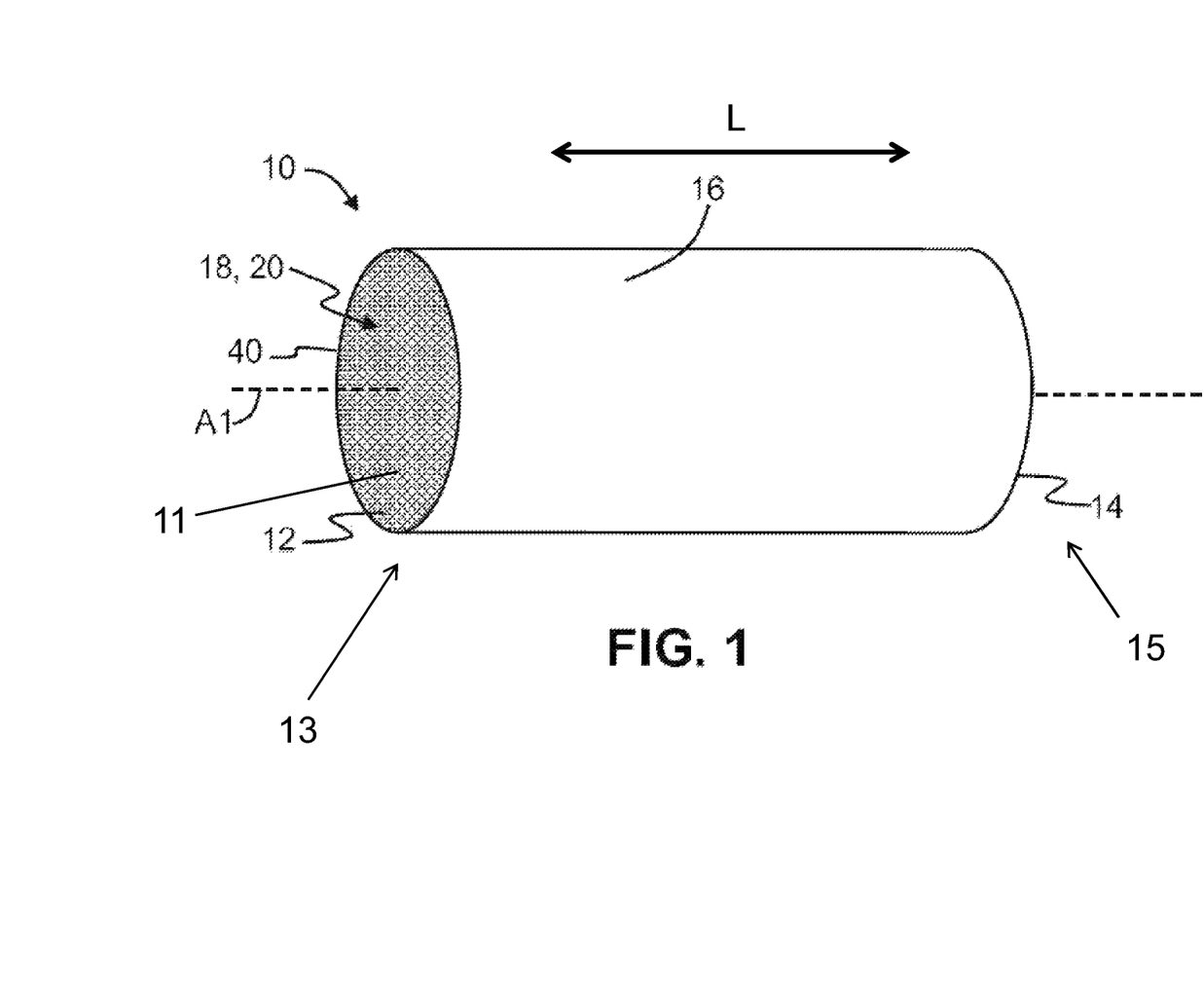
FIG. 1 is a side view of an example body comprising a structure comprised of walls that define a plurality of longitudinal channels.
Figure 2:
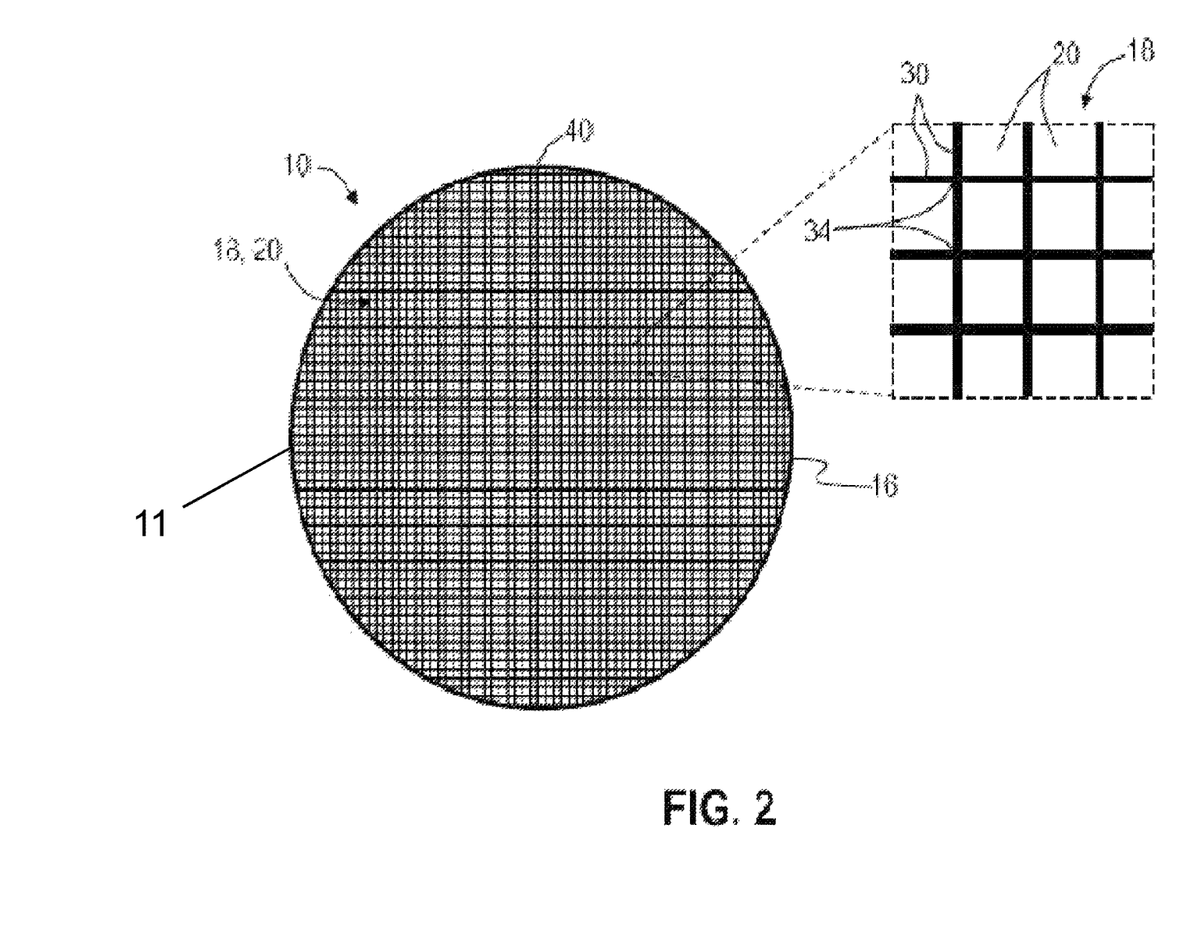
FIG. 2 is an end view, along with a close-up partial end view, of the example body of FIG. 1.

FIG. 1 is a side view of an exemplary body 10 comprising a structure 11 with longitudinal channels 20. FIG. 2 is a close-up, front-on view of the example body 10 of FIG. 1. The body 10 comprises a longitudinal axis A1, a first end 12, a first face 13, a second end 14, a second face 15 and an outer surface or outer peripheral surface 16. A longitudinal direction may be referenced as coincident with, or parallel to, longitudinal axis A1. Body 10 comprises structure 11 comprising walls 30 with wall intersections 34 that form a web 18 and define an array of cells or channels 20. Channels 20 can have shapes such as square (as schematically illustrated in FIG. 2), circular, triangular, hexagonal, octagonal, and/or other polyhedral shapes or combinations of shapes. Structure 11 may comprise an outer wall or skin 40 that may be an outer peripheral surface 16 of the body 10 as well as its overall outer shape. The close-up inset view of FIG. 2 schematically illustrates an example portion of well-formed walls 30 that define well-formed cells or channels 20.

Figure 3:
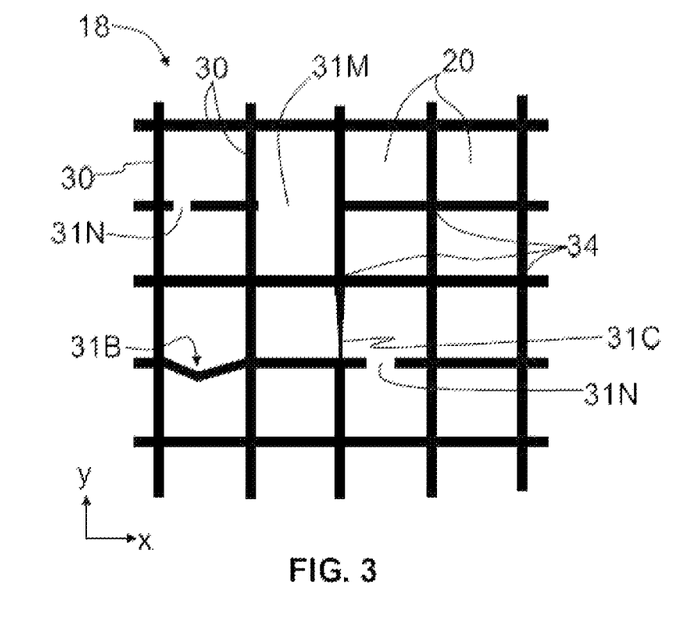
FIG. 3 is a close up view of a portion of an example web that illustrates a number of different types of wall defects that may occur in the structure of a body.

FIG. 3 is a schematic close-up end view of a portion of an example web 18 that illustrates a number of different types of wall defects or web defects. One type of wall defect is a non-knitter 31N, which occurs when one of walls 30 of a channel 20 is not completely formed and has a gap or space therein. A non-knitter 31N can be a particularly hard defect to locate and/or identify because the defect can be smaller than a single cell wall (which may be less than 4 mils or even less than 2 mils); such defects can adversely impact the structural integrity and/or performance of the body 10.

Another type of wall defect is a missing wall 31M, such as where substantially an entire wall of a given cell is absent. A missing wall 31M may also adversely impact the structural integrity and/or performance of the body 10.

Another type of wall defect is a bent or curved wall 31B. Yet another type of web defect is a chip 31C, i.e., a small missing piece missing from a wall 30 but that does not represent an actual hole in the wall. A chip 31C differs from a non-knitter 31N in that the latter extends deep into the web while the former is relatively shallow.

Figure 4:
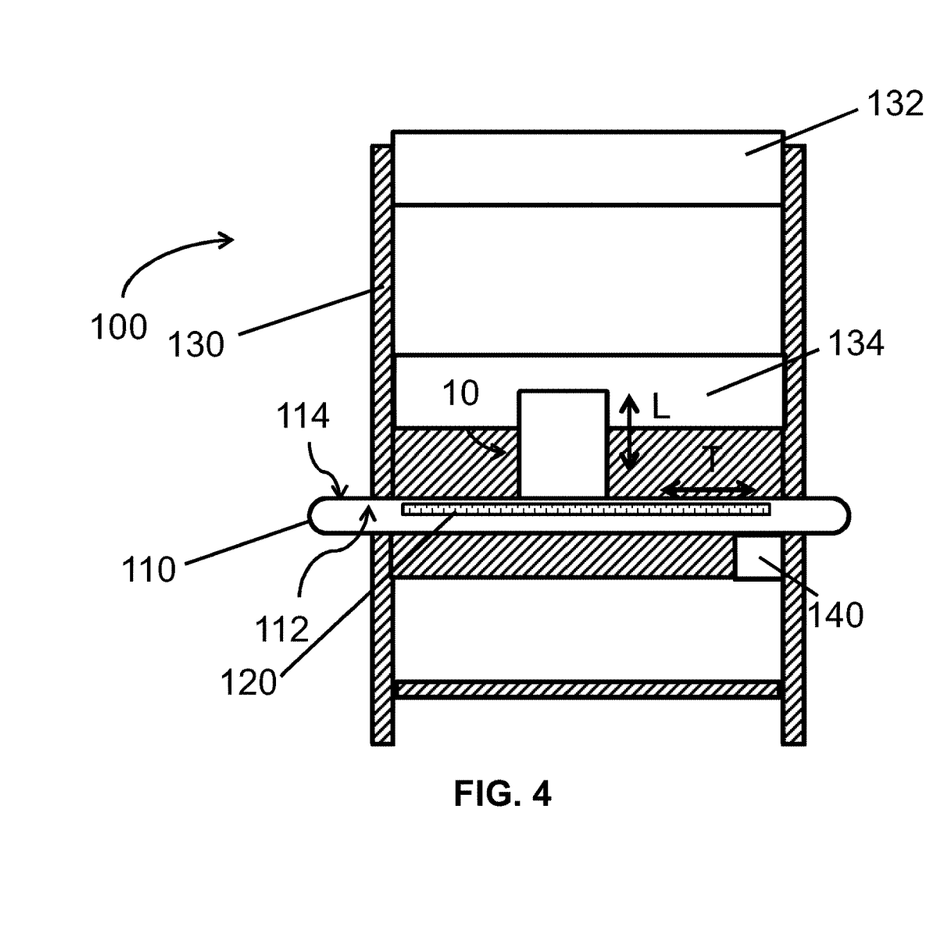
FIG. 4 is a front elevational schematic view of an inspection apparatus disclosed herein with an example body disposed thereon.
Figure 5:
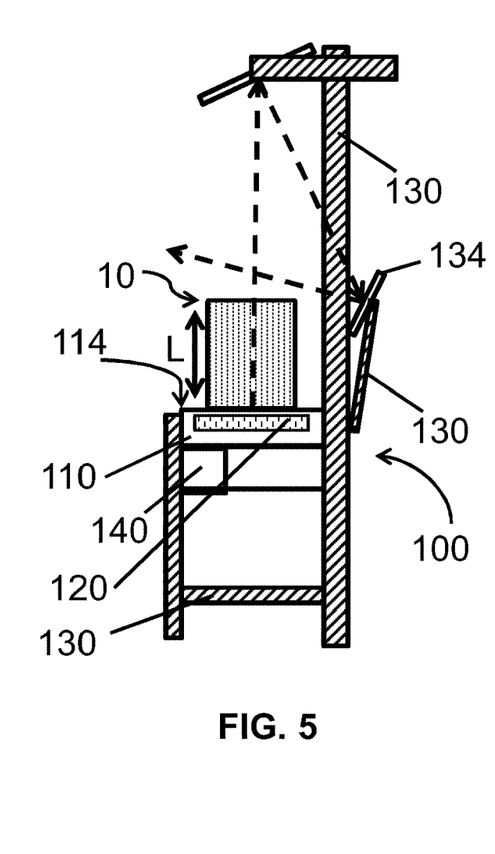
FIG. 5 is a side elevational schematic view of the inspection apparatus of FIG. 4, the example body being schematically depicted in cross-section to illustrate the passage of light therethrough.
Figure 6:
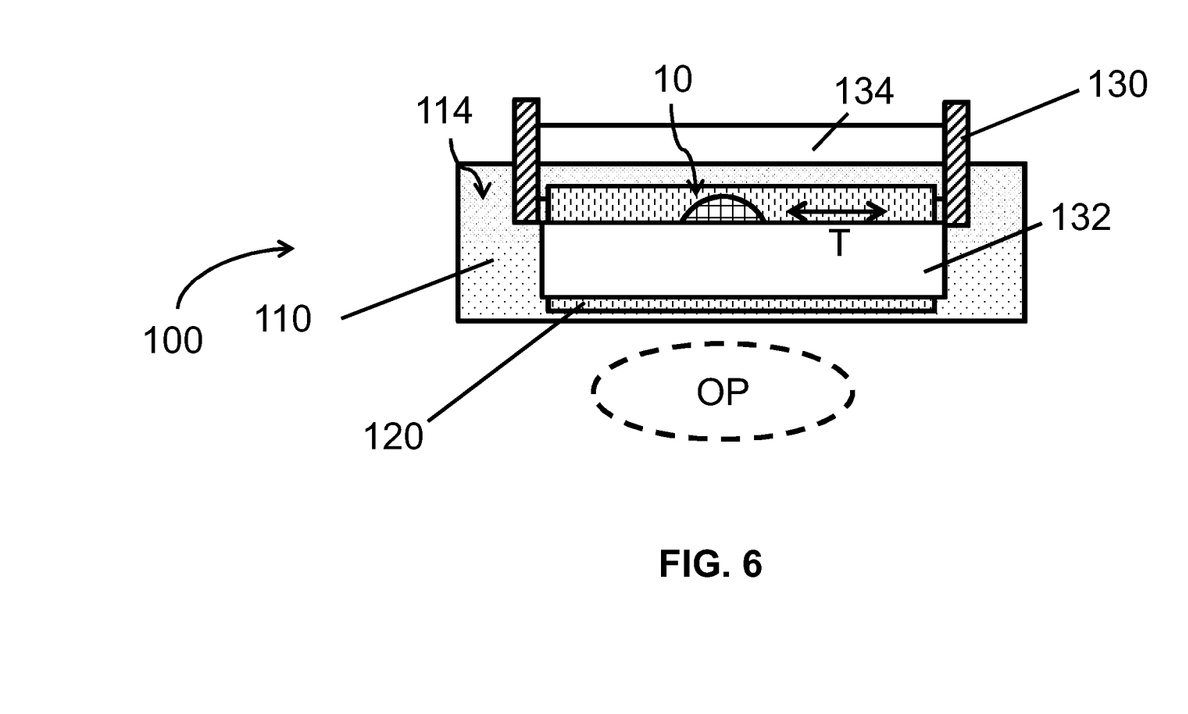
FIG. 6 is a top schematic view of the inspection apparatus of FIGS. 4-5, along with an example of an operator position from which an operator may inspect one or more bodies or structures with the inspection apparatus.

FIGS. 4-6 disclose herein and schematically illustrate an embodiment of an inspection apparatus 100 for inspecting a body 10 comprising a structure 11 comprised of walls 30 extending in a longitudinal direction L between a first end and a second end, the walls defining a plurality of longitudinal channels extending between first and second faces disposed at the first and second ends. An exemplary body 10 is shown in FIGS. 4-6 for illustrative purposes and does not form part of the apparatus.

Inspection apparatus 100 comprises: a translucent conveyor belt 110 comprising a backlight surface 112 and an opposing end supporting surface 114; and a light source 120 oriented to direct light "L" onto the backlight surface 112. Light source 120 may, for example, comprise one or more LED lights. Preferably, light source 120 is disposed behind (or under) one layer (i.e. a single layer) of belt material for example by being located between the upper and lower belt layers or belt paths such that the light only passes through one layer of belt material to reach the inspected article.

Belt 110 is preferably mounted on, or next to, a support structure 130. Belt 110 is preferably kept free from contact with any metal components or objects to avoid marking or other degradation of the translucent qualities of the belt. Apparatus 100 preferably further comprises a belt drive to control movement of the belt 110. Preferably, at least one mirror is oriented in relation to the path a body may take when disposed upon the belt ("travel path" T) to reflect an internally lighted image of the non-supported end of the body, the mirror preferably being mounted upon support structure 130. Preferably, the at least one mirror is adjustably mounted on the support structure, such as angularly adjustably mounted, to provide flexibility or variability in viewing angle of the image for the operator. In FIGS. 4-6, first mirror 132 is positioned above the travel path T. Thus situated, an operator may be positioned in an operator position "OP" located proximate the travel path with the ability to view the internally lighted image of the non-supported end of the body by looking upward, instead of having to bend and/or crane the neck to see down into the body 10 as the body is transported along the travel path. Apparatus 100 may optionally further comprise a second mirror 134 to further reflect the internally lighted image of the non-supported end of the body, the second mirror preferably being mounted upon support structure, or to another support structure in the proximity of the first mirror. Thus situated, an operator may be positioned in an operator position located proximate the travel path with the ability to view the internally lighted image of the non-supported end of the body by looking across the travel path, in some embodiments looking substantially horizontally across, in some embodiments looking downward and across, and in some embodiments looking upward and across, whereby the operator is spared having to bend and/or crane to see down into the body 10 as the body is transported along the travel path, or even to look substantially vertically upward, so as to achieve a more ergonomically favorable viewing.

The body can thus be moved during inspection. The moving comprises translating the body, such as in the travel direction illustrated in FIGS. 4-6. In some embodiments, the moving comprises translating the body past a light source; preferably the moving comprises transporting the body via translucent conveyor belt past a light source.

Preferably, diffuse light is directed into the body. For example, light source may emit non-diffuse light which passes through the translucent conveyor belt which acts as a diffuser such that diffuse light is directed into the body disposed on the translucent conveyor belt. In other embodiments, the light source can emit diffuse light which is directed through the translucent conveyor belt and into the body to be inspected. Optionally, the light emitted from the light source may be passed through a diffuser (other than the belt) to provide diffuse light, the diffuser being situated in the light path prior to passing through the belt.

Preferably, the body is disposed on a translucent conveyor belt during the emitting, inspecting, and moving.

Preferably, the body is oriented such that the longitudinal direction is vertical or substantially vertical. In these embodiments, either the first face or the second face may be the supported face, or face supported by the belt, and the opposite face is non-supported by the belt.

Preferably, the inspecting comprises viewing at least a portion of the walls from the second end, i.e. viewing an image provided by at least a portion of the lighted channels as seen from the second end, indirectly; in some embodiments, however, the inspecting may comprise directly viewing at least a portion of the walls from the second end.

In some embodiments, the inspecting comprises indirectly viewing at least a portion of the lighted channels from the second end, i.e. as seen from the second end.

In some embodiments, a view of the lighted channels from the second end is provided by a reflected image. In some embodiments, the reflected image is viewable from a viewing direction which is angularly offset from the longitudinal direction; for example, in some embodiments, the reflected image is viewable from a viewing direction which is angularly offset from the vertical direction. In some embodiments, the body is disposed between the reflected image and an operator viewing position, such that the reflected image is vertically and/or horizontally spaced away from the body; by spacing away the reflected image, i.e. by spacing away the image to be viewed for inspecting, the reflected image may appear smaller to an operator disposed at the operator viewing position as compared to a direct view or longitudinal view into the structure; thus, in some embodiments, an operator may be able to inspect a greater number of lighted channels simultaneously as compared to the number of lighted channels viewable directly without the spaced away reflected image; in some embodiments, the operator may be able to view all of the lighted channels as the body translates along with the conveyor belt, whereby movement (such as moving the operator's head or body in relation to the body or to the support structure or to the image) desired or required by the operator to conduct the inspection is reduced, or minimized, or even eliminated, whereby the inspection is facilitated, such as by more ergonomic conditions for the operator.

Thus, in some embodiments, the inspection may be further facilitated with the view provided by the walls and lighted channels being reflected at least once. In some embodiments, the view provided by the walls and lighted channels is reflected at least twice. In some embodiments, the view provided by the walls and lighted channels is reflected at least once to provide an improved ergonomic viewing angle. In some embodiments, the view provided by the walls and lighted channels is viewable at a location spaced away from the second end whereby an improved ergonomic viewing angle is provided.

In some embodiments, the structure is a honeycomb structure. In some embodiments, the structure is comprised of a porous material. In some embodiments, the structure is comprised of a porous ceramic material. In some embodiments, the structure is comprised of ceramic material. In some embodiments, the structure further comprises catalytic material. In some embodiments, at least a portion of the catalytic material resides within the walls.

In another set of embodiments, a method is disclosed herein of inspecting a body comprising a structure comprised of walls extending in a longitudinal direction between a first end and a second end, the walls defining a plurality of longitudinal channels extending between first and second faces disposed at the first and second ends, respectively, the method comprising conveying the body on a translucent conveyor belt past a light source to introduce diffuse light into the channels to provide lighted channels, and inspecting a view of the lighted channels from the second end.

The body may be disposed on the belt such that the channels are oriented vertically, as schematically illustrated in FIGS. 4-6.

In some embodiments, the lighted channels may be viewed directly from the second end for the inspecting. In some embodiments, the inspecting comprises indirect viewing of an image of the view of the lighted channels from the second end.

Preferably, the emitting, the inspecting, and the moving are all performed simultaneously.

In another set of embodiments, a method is disclosed herein of inspecting a body comprising a structure comprised of walls extending in a longitudinal direction between a first end and a second end, the walls defining a plurality of longitudinal channels extending between first and second faces disposed at the first and second ends, respectively, the method comprising: emitting light toward the first face and into the channels to provide lighted channels, inspecting a view of the lighted channels from the second end, and moving the body in a direction orthogonal to the longitudinal direction, wherein the emitting, the inspecting, and the moving are all performed simultaneously.

In some embodiments, the moving comprises translating the body. In some embodiments, the moving comprises translating the body past a light source. In some embodiments, the moving comprises transporting the body via a translucent conveyor belt past a light source.

In some embodiments, the emitting light comprises emitting a diffuse light.

In some embodiments, the body is disposed on a translucent conveyor belt. In some embodiments, the body is disposed on a translucent conveyor belt during the emitting, inspecting, and moving.

In some embodiments, the emitting light comprises passing the light through a diffuser to provide diffuse light.

In some embodiments, the body is oriented such that the longitudinal direction is vertical or substantially vertical.

In some embodiments, the inspecting comprises viewing the image indirectly. In some embodiments, the inspecting comprises indirectly viewing the lighted channels from the second end. In some embodiments, the view of the lighted channels from the second end is provided by a reflected image. In some embodiments, the reflected image is viewable from a viewing direction which is angularly offset from the longitudinal direction. In some embodiments, the reflected image is viewable from a viewing direction which is angularly offset from the vertical direction. In some embodiments, the reflected image is vertically spaced away from the body. In some embodiments, the body is disposed between the reflected image and an operator viewing position, such that the reflected image is horizontally spaced away from the body. In some embodiments, the reflected image appears smaller to an operator disposed at the operator viewing position as compared to a direct longitudinal view into the structure; in some of these embodiments, the image is reflected from a mirror which is vertically spaced away from the body, for example an upper mirror; in these embodiments, we have found that the upper mirror is preferably elevated at a sufficient distance above the body to permit efficient inspection of the body, otherwise the viewable area of illuminated channels is too small to efficiently inspect the body.

By spacing away the reflected image, i.e. by spacing away the image to be viewed for inspecting, the reflected image may appear smaller to an operator disposed at the operator viewing position as compared to a direct view or longitudinal view into the structure; thus, in some embodiments, an operator may be able to inspect a greater number of lighted channels simultaneously as compared to the number of lighted channels viewable directly without the spaced away reflected image; in some embodiments, the operator may be able to view all of the lighted channels as the body translates along with the conveyor belt, whereby movement (such as moving the operator's head or body in relation to the body or to the support structure or to the image) desired or required by the operator to conduct the inspection is reduced, or minimized, or even eliminated, whereby the inspection is facilitated, such as by more ergonomic conditions for the operator.

In some embodiments, the view provided by the walls and lighted channels is reflected at least once, whereby inspection is further facilitated. In some embodiments, the view provided by the walls and lighted channels is reflected at least twice, whereby inspection is further facilitated. In some embodiments, the view provided by the walls and lighted channels is reflected at least once to provide an improved ergonomic viewing angle. In some embodiments, the view provided by the walls and lighted channels is viewable at a location spaced away from the second end whereby an improved ergonomic viewing angle is provided.

Figure 7:
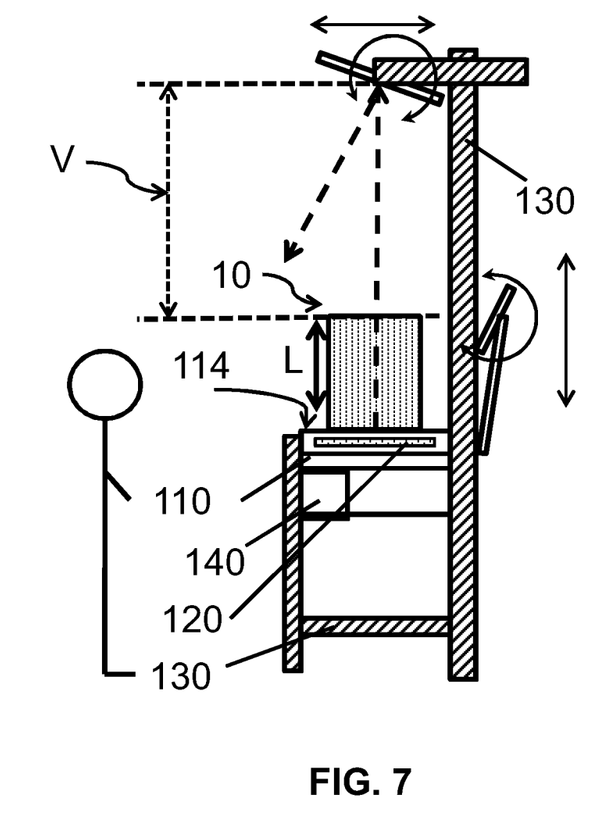
FIG. 7 is a side elevational schematic view of an exemplary inspection apparatus similar to FIG. 5 but configured such that an operator can view an image of the body from a first mirror.

FIG. 7 schematically illustrates an exemplary inspection apparatus disclosed herein wherein an operator can view an image of the body from a first mirror wherein the first mirror (here upper mirror) is spaced away from the body by vertical distance V. A second mirror may be optionally provided or omitted.

In some embodiments disclosed herein, the first mirror or the second mirror, or both, are adjustable, such as manually or mechanically controllably, to allow rotation about an axis such as its mounting axis, and/or translation with respect to its mount or frame, or combinations thereof, to provide flexibility in the possible configurations of the inspection system, such as to accommodate various sized bodies, or to accommodate various operator positions or orientations, and the like.

Figure 8:
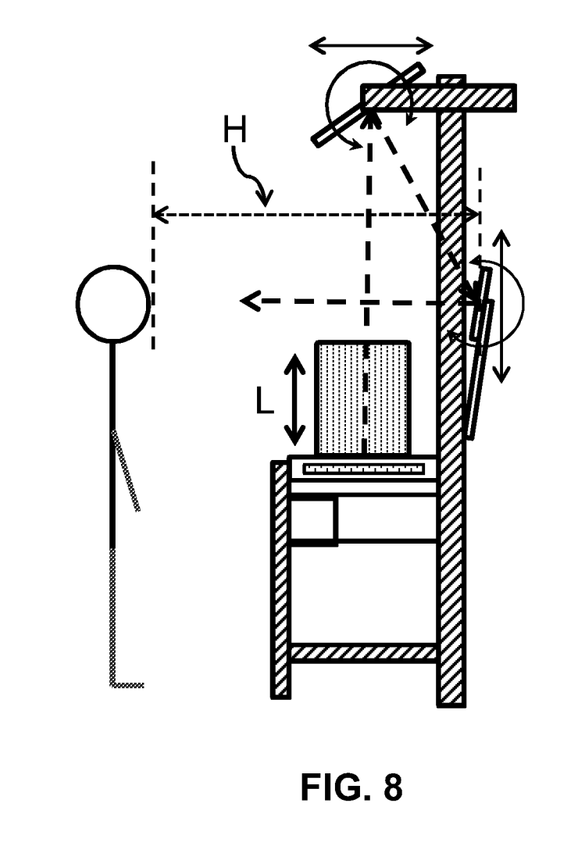
FIG. 8 is a side elevational schematic view of an exemplary inspection apparatus similar to FIG. 5 or FIG. 7 but configured such that an image of the body is reflected from a first mirror and a second mirror such that an operator can view an image of the body substantially horizontally from a distance H.

FIG. 8 schematically illustrates an exemplary inspection apparatus disclosed herein configured such that an image of the body is reflected from a first mirror and a second mirror such that an operator can view an image of the body substantially horizontally from a distance H. In some embodiments, having the image spaced away from the operator (e.g. by distance H in FIG. 8), a larger portion of the channels of a body may be viewed with minimized movement of the operator with respect to the body and/or the frame. In some embodiments, substantially all of the channels may be view by the operator from a single operator position.

Figure 9:
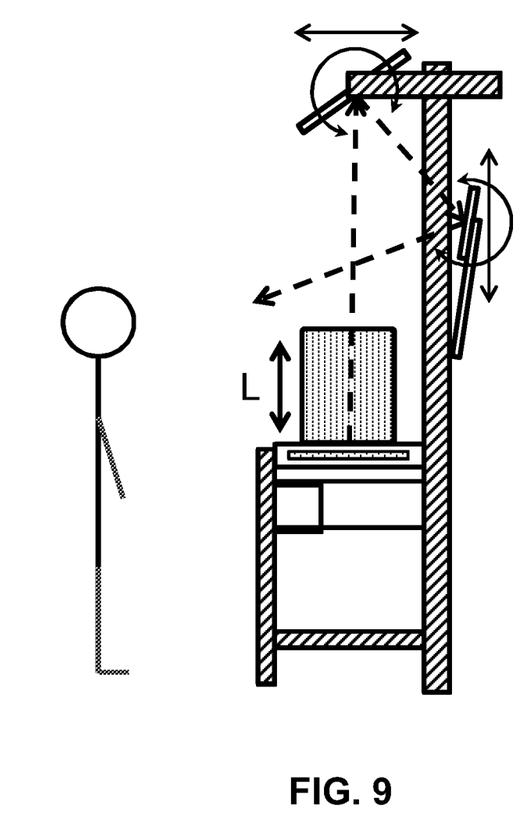
FIG. 9 is a side elevational schematic view of an exemplary inspection apparatus similar to FIG. 5 or FIG. 7 or FIG. 8 but configured such that an image of the body is reflected from a first mirror and a second mirror and downward toward an operator.

FIG. 9 schematically illustrates an exemplary inspection apparatus disclosed herein configured such that an image of the body is reflected from a first mirror and a second mirror and downward toward an operator.

Thus, the apparatus and methods disclosed herein may be utilized to inspect a body or bodies comprising a plurality of channels. The apparatus and methods may provide improved speed and/or accuracy, and may provide in addition and/or as result of, improved ergonomics. Furthermore, the apparatus and methods disclosed herein reduce the amount and/or degree of handling of the body or part to be inspected, for example as compared to known methods of lifting the body away from a conveyor belt, placing the body into an inspection device, and returning the body to the same or a different conveyor belt.

The methods may further comprise routing the body for destruction or repair, such as depending upon the assessment of the body during or after inspection, which may include, for example, removing the body from the conveyor belt before the body traverses the entire travel path provided by the translucent conveyor belt.

Inspection of a body may result in the identification of the location, character, type, and/or severity of one or more defects that may be present in or on the walls of the body. The existence of such defect or defects may be manifest by an irregularity or a disruption in the pattern in the image provided by the backlit walls.

It will be apparent to those skilled in the art that various modifications to the preferred embodiments of the disclosure as described herein can be made without departing from the spirit or scope of the disclosure as defined in the appended claims. Thus, the disclosure covers the modifications and variations provided they come within the scope of the appended claims and the equivalents thereto.

What is claimed is:

1. An inspection apparatus for inspecting a body comprising a structure comprised of walls extending in a longitudinal direction between a first end and a second end, the walls defining a plurality of longitudinal channels extending between first and second faces disposed at the first and second ends, respectively, the apparatus comprising:
    a translucent conveyor belt comprising a backlight surface and an opposing end supporting surface; and
    a light source oriented to direct light onto the backlight surface;
    wherein the light source and the belt are arranged to convey the body while directing diffuse light into the channels of the body in the longitudinal direction in the longitudinal direction.

2. The apparatus of claim 1 further comprising a belt drive to control movement of the belt.

3. The apparatus of claim 1 further comprising a mirror oriented to reflect an internally lighted image of a non-supported end of the body.

4. The apparatus of claim 3 further comprising a second mirror to further reflect the internally lighted image of the non-supported end of the body.

5. The apparatus of claim 1 wherein the structure is a honeycomb structure.

6. The apparatus of claim 1 wherein the structure is comprised of a porous material.

7. The apparatus of claim 1 wherein the structure is comprised of a porous ceramic material.

8. A method of inspecting a body comprising a structure comprised of walls extending in a longitudinal direction between a first end and a second end, the walls defining a plurality of longitudinal channels extending between first and second faces disposed at the first and second ends, respectively, the method comprising:
   emitting light toward the first face in the longitudinal direction and into the channels to provide lighted channels,
   inspecting a view of the lighted channels from the second end, and
   moving the body in a direction orthogonal to in the longitudinal direction, wherein the emitting, the inspecting, and the moving are all performed simultaneously, wherein the moving comprises translating the body.

9. The method of claim 8 wherein the moving comprises translating the body past a light source.

10. The method of claim 8 wherein the moving comprises transporting the body via a translucent conveyor belt past a light source.

11. The method of claim 8 wherein the emitting light comprises emitting a diffuse light.

12. The method of claim 8 wherein the body is disposed on a translucent conveyor belt.

13. The method of claim 8 wherein the body is disposed on a translucent conveyor belt during the emitting, inspecting, and moving.

14. The method of claim 8 wherein the emitting light comprises passing the light through a diffuser to provide diffuse light.

15. The method of claim 8 wherein the body is oriented such that the longitudinal direction is vertical or substantially vertical.

16. The method of claim 8 wherein the inspecting comprises viewing the image indirectly.

17. The method of claim 8 wherein the inspecting comprises indirectly viewing the lighted channels from the second end.

18. The method of claim 8 wherein the view of the lighted channels from the second end is provided by a reflected image.

19. A method of inspecting a body comprising a structure comprised of walls extending in a longitudinal direction between a first end and a second end, the walls defining a plurality of longitudinal channels extending between first and second faces disposed at the first and second ends, respectively, the method comprising:
   conveying the body on a translucent conveyor belt past a light source;
   emitting diffuse light from the light source into the channels in the longitudinal direction to provide lighted channels, and
   inspecting a view of the lighted channels from the second end, wherein the body is disposed on the belt such that the channels are oriented vertically, wherein the inspecting comprises indirect viewing of an image of the view of the lighted channels from the second end;
   wherein the emitting, the inspecting, and the conveying are all performed simultaneously.

* * * * *

UNITED STATES PATENT AND TRADEMARK OFFICE
CERTIFICATE OF CORRECTION

PATENT NO. : 10,458,925 B2
APPLICATION NO. : 15/213680
DATED : October 29, 2019
INVENTOR(S) : Andrew Paul Courtney et al.

Page 1 of 1

It is certified that error appears in the above-identified patent and that said Letters Patent is hereby corrected as shown below:

In the Claims

In Column 8, Line 56, Claim 1, after "body" delete "in the longitudinal direction".

Signed and Sealed this
Third Day of March, 2020

Andrei Iancu
*Director of the United States Patent and Trademark Office*